United States Patent [19]

Bisagni et al.

[11] 4,260,630
[45] Apr. 7, 1981

[54] SKIN DISEASES

[75] Inventors: Emile R. Bisagni; Dietrich Averbeck; Ethel Moustacchi, all of Orsay; Francois Zajdela, Anthony, all of France

[73] Assignee: Agence Nationale de Valorisation de la Recherche (ANVAR), Neuilly sur Siene, France

[21] Appl. No.: 828,866

[22] Filed: Aug. 29, 1977

[51] Int. Cl.³ ............................................. A61K 31/35
[52] U.S. Cl. ..................................................... 424/283
[58] Field of Search ........................................ 424/283

[56] References Cited
PUBLICATIONS

Pathak et al., 1974, Sunlight and Man ed., pp. 335–368, University Press, Tokyo.

Primary Examiner—Jerome D. Goldberg
Attorney, Agent, or Firm—Berman, Aisenberg & Platt

[57] ABSTRACT

Skin diseases such as psoriasis, namely: psoriasis punctata, herpes simplex and mycosis fungoides are treated by administering (either topically or orally) to an afflicted subject an effective amount of monofunctional derivative of the formula

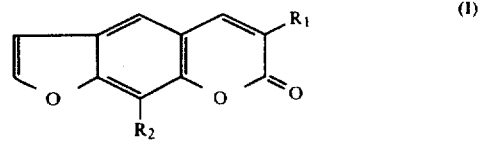

wherein $R_1$ is —$COOR_3$ or —CN; $R_2$ is —H or —$CH_3$; and $R_3$ is —H, —$CH_3$ or —$CH_2CH_3$.

16 Claims, No Drawings

SKIN DISEASES

BACKGROUND OF THE INVENTION

1. Field of the Invention

The present invention relates to the field of treating skin diseases. It particularly concerns a new method and composition for the treatment of psoriasis namely: psoriasis punctata, herpes simplex and mycosis fungoides, microbian eczema, acne, and, more generally, of benign or malignant skin proliferations.

2. Description of the Prior Art

Psoriasis is a rather frequent dermatosis of unknown etiology, with chronic evolution, and characterized by red, more or less wide, spots, well defined and covered by dry, numerous and brittle scales.

A recently-developed method for curing such diseases consists of administering certain furocoumarins (commonly called psoralens) either orally or topically. Of the active furocoumarins, 8-methoxypsoralen (hereinafter and usually referred to as 8-MOP) is used most widely in conjunction with exposure to near-ultraviolet light (around 365 nm). This treatment is known as PUVA-therapy.

This method provides good results but presents significant drawbacks. One of the most severe drawbacks, even if skin cancer had not been observed on patients previously treated with psoralen, is the potential danger of further involvement such as a skin cancer. This aspect has to be considered, as psoralens are powerful mutation inducers and some experiments effected on mice have shown that (after either topical or local administration) tumors were obtained on 100% of mice (GRIFFIN A. C., R. E. HAKIM and J. KNOX, *J. Invest. Dermatol.* 31/289–295,1958). Similar results were also indicated by F. URBACH, *J. Invest. Dermatol.* 32/373–378/1959. A more complete experiment was accomplished on two issues of hairless mice (JKH, hairless and HRS/J/AnC hairless) D. D. GREEBE, R. D. LEY et R. J. M. FRY in *Photochem. and Photobiol.* 25/269–276/1977 and confirmed the high cancerogenic power of 8-MOP in combination with U.V. radiation. Complementary results concerning this cancerogenic character of 8-MOP is provided hereinafter.

An object of this invention is to find products capable of curing previously-mentioned diseases without the noted drawbacks.

Complementary burning or blistering of the skin, dermatosis, gastric irritation, nausea, nervousness, insomnia and depression may occur with average doses of 8-MOP.

See, for example, "The Merck Index", Seventh Edition, p. 670; and M. A. Pathak; D. M. Kramer and T. B. Fitzpatrick (1974) in "Sunlight and Man", ed. M. A. Pathak, L. C. Harber, M. Seiji, A. Kukita, pp. 335–368, University Press, Tokyo.

The last-cited document indicates that the ability to sensitize cutaneous tissue to light appears to be a unique characteristic of the psoralen molecule having the following formula:

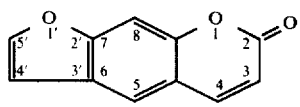

Complementary, it was stated that psoralen and methyl-substituted psoralen derivatives (substitution at 4-,4'-,5'- and 8-positions) are found to be most effective photo-sensitizers. Substitution by methyl or other groups at the 3 positions, however, does reduce the photosensitizing ability significantly.

For example, compounds such as 3,5',8-trimethylpsoralen, 3-methylpsoralen, 3,4,5',8-tetramethylpsoralen, 3,4-dibenzo-5,8-dimethylpsoralen, 3,4-cyclohexeno-5',8-dimethylpsoralen, and 3-n-butyl-4,5',8-trimethylpsoralen were found to be inactive or to induce very weak photosensitivity. More particularly, a psoralen derivative, such as 3-carboethoxypsoralen was mentioned as being completely inactive (table 2, p. 342) in view of its lack of photosensitizing ability.

It has been suggested that the sensitizing effect (*in vivo* and *in vitro*) of some furocoumarins was due to photoreactions with pyrimidine bases of nucleic acids.

Thus furocoumarins of the psoralen type have two photo-reactive sites, the 3,4 and the 4',5' double bonds, as indicated in the previously-noted formula. In the presence of 365 nm light mono-adducts with pyrimidines are formed, i.e. $C_4$-cyclo addition products involving the 5,6 double bond of pyrimidine are formed (2–4). Moreover, DNA cross-links are detected by several methods including the melting and renaturation pattern of treated DNA. It is assumed that the 3,4 and 4',5' double bonds of the psoralen derivatives are both involved in the formation of cross-links between pyrimidines of opposite DNA strands.

Up to recent years it was generally assumed that the main photosensitizing effects produced by psoralens were due to their ability to form cross-links in cellular DNA [Cole R. S.: "Light-induced Cross-linking of DNA in the Presence of a Furocoumarin", *Biochim. Biophys. Acta*, (Amst.) 217, 30–39 (1970)].

Consequently, it was commonly believed that it should not be possible to use monofunctional (that is to say 3,4- or 4',5'-substituted furocoumarins plus U.V. radiation for the treatment of skin diseases since such compounds do not form cross-linkages in DNA. This was confirmed by commonly-used tests in which the activity of psoralen derivatives with regard to skin diseases was estimated by observing the appearance of skin erythema after application of the product plus near-U.V. irradiation. The absence of an erythema was considered as proof for the absence of activity. Indeed some of the known mono-functional furocoumarins did not provocate an erythema.

GENERAL DESCRIPTION OF THE INVENTION

Surprisingly, it is possible to use monofunctional derivatives of the formula

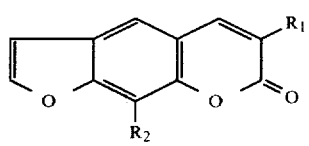

[wherein $R_1$ is a carboxy group of the formula $-COOR_3$ or CN; $R_2$ is $-H$ or $-CH_3$; and $R_3$ is $-H$, $-CH_3$ or $-CH_2-CH_3$] for the treatment of skin diseases.

Among the compounds corresponding to this general formula the preferred psoralen derivative 3-carboethoxypsoralen (3-CPs), i.e. compound (I) in which $R_1 = -COOCH_2CH_3$, $R_2 = H$, is a photoactive product which exhibits particularly good characteristics in the treatment of skin diseases, such as psoriasis or other previously-mentioned skin diseases.

The invention also relates to new compounds of the formula

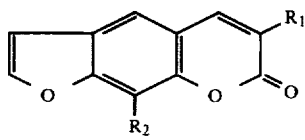

wherein $R_1$ is a carboxy group of the formula —$COOR_3$ or —CN; $R_2$ is H or $CH_3$; and $R_3$ is —H, —$CH_3$ or —$CH_2CH_3$.

Syntheses of psoralen derivatives have previously been described, for example, by Leonard R. Worden et al. in the *Journal of Organic Chemistry*, Vol. 84, No. 8, August 1969 p. 2311–2313.

Another process for the production of psoralen and its derivatives was published by Pierre Queval and Emile Bisagni in *EUR. J. MED. CHEM-CHIMICA THERAPEUTICA*, MAY-JUNE 1974–9, No. 3, 335–340. These two documents are herein incorporated by reference.

The new method for treating skin diseases according to the present invention consists of administering (orally or topically) an effective amount of a compound of formula (I) and submitting the patient to near-U.V. light.

It has now been found that for topical application ointments or solutions may be used, containing from about 0.5% to about 4% (on a weight basis) of the therapeutically effective compound concentrations of about 2% to 4% are preferred. More particularly, a solution or ointment containing about 2% by weight of the compound was found appropriate.

As carriers for the solutions or ointments according to the invention one may use all commonly-employed carriers which are well known to men skilled in the art. Examples of such carriers are cited by Schäfer and al. in *Archiv. of Dermatology* (1976), this document being herein incorporated by reference.

It is, of course, also possible to incorporate the compounds of the present invention in other compounds, solutions or ointments, or to add perfumes, dyes or preserving agents or any other commonly-used compounds. It is also possible to combine two or more photosensitizing agents.

For oral administration, quantities comprised between about 1 mg and about 2 mg per kg of weight of the patient are particularly preferred.

As previously mentioned, the method of treatment comprises irradiation by near-ultraviolet-light with a spectrum including or mainly consisting of the wavelength of 365 nm. As will be explained hereinafter, the cumulative dose of irradiation may be very high, for example as high as 10 $J/cm^2$ or 15 $J/cm^2$ or more. A dose of about 5 $J/cm^2$ to 15 $J/cm^2$ already gives good results. Nevertheless doses up to 20 $J/cm^2$ may be used for a short period of time.

Hereinabove, it was mentioned that the formation of an erythema was usually considered to be bound to the therapeutic efficiency of psoralen derivatives, such as 8-MOP, which are able to form DNA crosslinks.

In contrast, it has now been discovered that the mono-functional derivatives of formula I provoke absolutely no erythema, neither immediate nor postponed. No skin injury, neither macro- nor microscopic, was observed on patients. It will be readily apparent to men skilled in the art that this property is a very unique one for compounds of the psoralen family. In addition, the present invention includes compounds which do not show the strong tanning effect as is produced by 8-MOP. Thus, undesirable cosmetic side effects appear to be absent. Consequently, these compounds are of great interest since, in contrast to 8-MOP, they permit subsequent treatment at short-time intervals for example twice a day over prolonged periods of time without any sun-burnlike injury to the skin. Short treatment intervals are not indicated when using 8-MOP since it can cause violent erythemal reactions in the skin.

Complementally, it is known that a psoralen derivative, such as 8-MOP, causes a decrease of the lymphocytes in circulating blood in the course of a therapeutic treatment. By using a compound (I) according to the invention, no such decrease of lymphocytes was noted.

The surprising photosensitizing properties of compounds (I) on which the present invention is based are revealed by using the yeast, *Saccharomyces cerevisiae;* the biological test with yeast has proved to be particularly useful for the detection of the biological activity of new chemicals. In the following data concerning this system are presented.

In order to determine the biological effects and repair of lesions photoinduced by compounds (I) of the invention, the photoreactivity, the lethal and genetic effects in yeast (taken as a model eucaryotic system) of 3-CPS was studied and compared to those of 8-MOP. It was found that bifunctional furocoumarins, such as psoralen or 8-MOP, are at least 10 fold more effective in inducing nuclear back mutations (his− to His+) than monofunctional furocoumarins (such as 3-CPs or angelicin) plus 365 nm light (near UV) or 254 nm ultraviolet light (far UV) alone.

When compared at the same survival level (10%), monofunctional furocoumarins are very efficient inducers of cytoplasmic "petite" mutations, 3-CPs is the most reactive compound. The previously-mentioned bifunctional furocoumarins induce cytoplasmic "petite" mutations with less efficiency than the monofunctional furocoumarins under the same conditions. In comparison to psoralen, 8-MOP is less reactive.

With regard to damage of nuclear DNA it was consequently presumed that monofunctional damage may be more easily reparable than bifunctional damage. This observation is important in view of the widely accepted correlation between mutagenic activity chemicals and their ability to induce a cancerogenic process.

MATERIALS AND METHODS USED

Yeast strains

A wild-type strain 211-1aM (29) of *Saccharomyces cerivisiae* was used, and the following mutants derived from it: S24-12c $rad_{2-20}$ deficient in excision repair and S25-13b $rad_{9-4}$ likely to be blocked in a recombinational repair pathway; a double mutant S 2057NL-24 $rad_{2-20}$ -$rad_{9-4}$ clone B was obtained by tetrad analysis of a heterozygote $$\text{diploid } ( \frac{+}{rad_{2-20}} \quad \frac{rad_{9-4}}{+} ).$$

Media, culture and treatment conditions, irradiation procedure:

The media and culture conditions used were as described in D. Averbeck, E. Moustacchi, (1975) *Biochim. Biophys. Acta*, 395, 393-404.

$10^6$ cells/ml in saline (0.9% NaCl) were treated for 30 minutes with the drugs at a final concentration of 10 μg/ml and 1.2% ethanol present.

A Philips HPW 125 culot Edison high pressure mercury lamp was used with maximal output at the wavelength 365 nm. The irradiation dose measured by actinometry was 10 J/m² per sec., using the following set up: 10 ml of actinometer solution (or the cell suspension, usually $1 \times 10^6$ cells/ml), stirred continuously by a magnetic stirrer, were irradiated at room temperature in an open Petri dish of 10 cm diameter at a distance of 10 cm from the center of the light bulb which was mounted horizontally. A 2 mm thick pyrex glass sheet (20×25 cm) was placed in the center of the light beam to cut out UV light of wavelength below 340 nm. Overheating was prevented either by a continuous flow of compressed air between the light bulb and the glass or by a pyrex glass water filter of 3 cm total thickness. An accumulative irradiation dose was given to the same sample. After each dose 0.1 ml of irradiated cell suspension was taken, diluted and aliquots plated.

Biochemical measurement of the photobinding of 3-CPs and 8-MOP to nucleic acids

These determinations were done *in vitro* and *in vivo*. According to Musago and Rodighiero, (1970) *Photochem. Photo-biol.* 11,27-35, and Dall'Acqua et al., (1969) *Z. Naturf.*, 24b, 667-671, 3 ml samples of filtered (Millipore SM5) calf thymus DNA (Sigma, type I) at a 0.1% concentration in phosphate buffer (pH 7, 0.1 M) were irradiated at 365 nm in the presence of several concentrations of tritiated 3-CPs or 8-MOP. The thickness of the irradiated sample was 1 mm. After irradiation, the solution was diluted by a factor of 2, and NaCl was added to a final concentration of 1 M. The DNA was precipitated with 2 volumes of cold pure ethanol. The samples were left overnight in the cold at −20° C. The precipitate was then washed by centrifugation three times with 3 ml of 70% ethanol and redissolved in 3 ml of water. The DNA recovery was checked by determination of the optical density of the solution at 260 nm.

The radioactivity of an aliquot (0.1 ml) of this solution was measured in 5 ml of scintillation mixture (Nuclear Entreprise, Ltd., Edinburgh, Scotland, NE 250).

For the *in vivo* determinations stationary phase cells of the haploïd wild type strain N 123 were prepared as previously described. One minute before irradiation, a given amount of radioactive-labelled 3-CPs or 8-MOP was added to 2 ml of cell suspension at $5 \times 10^7$ cells/ml. The final concentration of 8-MOP and of 3-CPs was as indicated in tables 1 and 2.

TABLE 1

Binding of 3-$^{14}$C-3-CPs to yeast nucleic acids in vivo
The amount of DNA per cell was assumed to be $5 \times 10^{-8}$ μg and the amount of RNA per cell $250 \times 10^{-8}$ μg

| Duration of treatment (min) | Dose of 365 nm light in ergs. mm$^{-2}$ × 10$^4$ | cpm for 10$^8$ cells | μg 3-CPs/ μg DNA × 10$^{-2}$ | Molecules 3-CPs/μg DNA × 10$^{14}$ |
|---|---|---|---|---|
| (a) Binding to DNA | | | | |
| 5-60 | — | 67.75 | 0.05 | 0.012 |
| 5 | 6.3 | 5030.5 | 3.9 | 0.92 |
| 10 | 12.6 | 9409 | 5.7 | 1.34 |
| 15 | 18.9 | 11386.5 | 9 | 2.1 |
| 20 | 25.2 | 15650.2 | 12.3 | 2.8 |
| 30 | 38.8 | 15307 | 12 | 2.8 |
| 40 | 50.4 | 14248 | 11 | 2.6 |
| 60 | 75.6 | 16476 | 10 | 2.3 |
| (b) Binding to RNA | | | | |
| 5-60 | — | 1285 | 0.01 | 0.0023 |
| 5 | 6.3 | 7130 | 0.056 | 0.0130 |
| 10 | 12.6 | 11040 | 0.086 | 0.020 |
| 15 | 18.9 | 14170 | 0.11 | 0.026 |
| 20 | 25.2 | 18780 | 0.15 | 0.034 |
| 30 | 37.8 | 25380 | 0.20 | 0.046 |
| 40 | 50.4 | 29240 | 0.23 | 0.053 |
| 60 | 75.6 | 31730 | 0.25 | 0.058 |

TABLE 2

Binding of $^3$H-8-MOP to yeast nucleic acids

| Duration of treatment (min) | Dose of 365 nm in light ergs. mm$^{-2}$ × 10$^4$ | cpm for 10$^8$ cells | μg 8-MOP/ μg DNA × 10$^{-2}$ | Molecules 8-MOP/μg DNA × 10$^{14}$ |
|---|---|---|---|---|
| (a) Binding to DNA | | | | |
| 15-120 | — | 404.75 | 0.126 | 0.034 |
| 15 | 18.9 | 1161 | 0.36 | 0.10 |
| 30 | 37.8 | 1474 | 0.46 | 0.13 |
| 60 | 75.6 | 2805 | 0.86 | 0.24 |
| 90 | 113.4 | 5582 | 1.72 | 0.48 |
| 120 | 151.2 | 5572 | 1.72 | 0.48 |
| (b) Binding to RNA | | | | |
| 15-120 | — | 3805 | 0.12 | 0.033 |
| 15 | 18.9 | 7400 | 0.228 | 0.064 |
| 30 | 37.8 | 12920 | 0.40 | 0.11 |
| 60 | 75.6 | 23580 | 0.73 | 0.20 |
| 90 | 113.4 | 34150 | 1.05 | 0.29 |
| 120 | 151.2 | 44060 | 1.36 | 0.38 |

2 ml cell suspensions were exposed to several doses of 365 nm light. In parallel, non irradiated samples were incubated for the same periods. Immediately after incubation and/or irradiation, the samples were centrifuged and the pellet was washed 3 times with 5 ml of saline (0.9% NaCl). The washed cell pellet was resuspended in 1 ml of saline and 1 ml of 2 N NaOH was added in order to hydrolyze the RNA. The suspension was incubated overnight in the dark at room temperature, then cooled down on ice, and 2 ml of 50% TCA were added slowly. The samples were left 20 minutes on ice and the precipitated DNA was filtered on a glass fiber filter disc (Whatman GF/A, 2.1 cm diameter). In some cases the filtrate containing the acid-soluble material was kept aside, and the radioactivity of an aliquot added to 5 ml of NE250 scintillation mixture measured. The precipitate was washed 3 times with 5 ml of 5% cold TCA and 5 ml of 70% ethanol. The filters were then dried and the radioactivity measured in plastic counting vials containing 5 ml of scintillation mixture (NE 250) in a Tricarb Packard scintillation spectrophotometer.

Measurement of the melting and reassociation characteristics of yeast DNA:

Yeast DNA was isolated and purified in a CsCl gradient according to Williamson et al., (1971) *Biochim. Biophys. Acta*, 238, 369-374. The fractions containing the nuclear DNA were pooled and dialysed against a 0.1 M, pH 7 phosphate buffer. Various amounts of DNA (1 to 10 μg/ml) were irradiated with several doses of 365 nm light in the presence or absence of different concentrations of 8-MOP or 3-CPs. Unirradiated samples of DNA with or without the drugs were taken as references. The melting and reassociation characteristics were determined with the measuring device and the computer program of REISS and MICHEL, (1974) *Anal. Biochem.*, 62, 499–508; the procedures adopted were the same as they described.

RESULTS

A—Photobinding of 3-CPs to nucleic acids (1) *In vitro:*

The binding capacity of 3-CPs to native calf thymus DNA after irradiation at 365 nm as compared to 8-MOP is shown in tables 3 and 4.

TABLE 3

Binding of 3-$^{14}$C-3-CPs to calf thymus DNA
The concentration of 3-$^{14}$C-3-CPs was $6 \times 10^{-5}$M

| Duration of treatment in minutes | Dosage of 365 nm light in ergs. mm$^{-2}$ × 10$^4$ | cpm/μg DNA | μg 3-CPs/μg DNA | Binding yield 3-CPs molecules/ nucleotide |
|---|---|---|---|---|
| 0–60 incubation | | 0.21 | 0.009 × 10$^{-3}$ | 1/88 × 10$^3$ |
| 15 | 18.9 | 3.29 | 0.14 × 10$^{-3}$ | 1/5.6 × 10$^3$ |
| 30 | 37.8 | 4.25 | 0.18 × 10$^{-3}$ | 1/4.4 × 10$^3$ |
| 45 | 56.7 | 4.30 | 0.18 × 10$^{-3}$ | 1/4.4 × 10$^3$ |
| 60 | 75.6 | 3.10 | 0.13 × 10$^{-3}$ | 1/6.1 × 10$^3$ |

TABLE 4

Binding of $^3$H-8- MOP to calf thymus DNA
The concentration of $^3$H-8-MOP was $7.5 \times 10^{-5}$

| Duration of treatment in minutes | Dose of 365 nm light in erg. cm$^{-2}$ | cpm/μg DNA | μg 8-MOP μDNA | Binding yield 8-MOP molecules/ nucleotide |
|---|---|---|---|---|
| 0–180 incub. | | 0.24 | 0.031 × 10$^{-4}$ | 1/1.8 × 10$^4$ |
| 30 | 37.8 | 56.3 | 7.3 × 10$^{-4}$ | 1/900 |
| 60 | 75.6 | 95.7 | 12.4 × 10$^{-4}$ | 1/532 |
| 90 | 113.4 | 118.8 | 15.4 × 10$^{-4}$ | 1/428 |
| 120 | 151.2 | 131.5 | 17.1 × 10$^{-4}$ | 1/386 |
| 180 | 226.8 | 198.5 | 25.8 × 10$^{-4}$ | 1.256 |

The binding of the two furocoumarins (observed in controls only) held in the dark for time intervals equal to those of the corresponding irradiated samples was low (0 to 60 minutes incubation in the dark, table 3; 0 to 180 minutes incubation in the dark, table 4).

The binding of 3-CPs increases rapidly with doses up to 3780 J/m² and reaches a plateau followed by a decline with increasing dose. The same is true for 8-MOP, however, the saturation is reached for a higher dose. In spite of the high concentration (0.1%) of DNA used, there is an excess of furocoumarin molecules, i.e. at the highest doses of 365 nm light not all molecules are bound. The photoreactivity of 3-CPs with native DNA is about 5 times lower than that of 8-MOP calculated on the initial part of the photoreaction.

(2) *In vivo:*

The binding capacity of 3-CPs and 8-MOP to yeast nucleic acids after treatment with 365 nm light is shown in tables 1 and 2. In the controls incubated in the dark for 50 minutes, the binding with DNA is negligible for 3-CPs (around 10%) but is significant for 8-MOP (about 35%). However, for the two compounds, the binding in the dark with RNA is relatively significant (20% for 3-CPs and 50% for 8-MOP). These percentages refer to the binding in controls relative to that obtained by the lowest dose of irradiation.

The binding of 3-CPs with DNA and RNA increases linearly with 365 nm light doses up to $25.2 \times 10^3$ J/m² and then levels off. With the conditions used, the amount of 3-CPs linked to DNA is about the same as that bound to RNA per cell. It is clear from tables 1 and 3 that 3-CPs is capable of binding to DNA *in vitro* and *in vivo*. This binding is higher in the *in vivo* condition than *in vitro*.

When cells are treated with an equimolar concentration of 8-MOP, the binding with DNA and RNA increases linearly in the range of light doses used. The amount of 8-MOP linked to RNA is about 5 times higher than that bound to DNA per cell. As for 3-CPs the binding of 8-MOP to DNA is much higher in the *in vivo* condition than *in vitro*.

It is important to note that 3-CPs binds to DNA much more efficiently than 8-MOP. The difference in photoreactivity with DNA is within a factor of 20. However, the photoreactivity with RNA differs by a factor of 3.4.

In spite of a high affinity of 3-CPs to cellular DNA the survival level is still relatively high as compared to that for 8-MOP. For instance, at the concentration used, 5-minute irradiation results in $10^{-1}$ survivors for 3-CPs and $10^{-5}$ survivors for 8-MOP. This already implies that the 3-CPs plus 365 nm light induced lesions are less relevant to cell killing than those induced by 8-MOP plus light.

(3) Heat denaturation and reassociation pattern of yeast DNA treated in vitro with 3-CPs or 8-MOP plus 365 nm light:

The cross-links formation of the two furocoumarins with native yeast DNA was tested by measuring the denaturation and renaturation pattern.

In the presence of 8-MOP plus 365 nm light it was established that a fraction of the DNA is capable to renature. On the contrary, such a reassociation was not found in the case of 3-CPs at least in the range of doses and concentrations used. Since this capacity to renature is taken as an indication for the presence of cross-links between two DNA strands, it was possible to conclude that 3-CPs plus 365 nm light does not induce cross-links in DNA.

From the molecular structure of 3-CPs this molecule is likely to react with DNA by monofunctional binding.

B—Effects of 365 nm light alone or 3-CPs, uptake and removal of the drug.

Since high doses of 365 nm light are needed to induce a killing effect in Saccharomyces cells in the presence of 3-CPs, the effects of 365 nm light alone were measured for doses up to 7500 J/m². It was established that, in the range of doses used for the biological experiments, there was only a small lethal effect of 365 nm light alone. Taking into account the standard errors of the surviving fraction (±10%) and the fact that part of the light energy is absorbed by the drug itself, the effect of 365 nm light alone has been neglected in the experiments. In wild-type and rad$_{9-4}$ cells the killing and cytoplasmic "petite" induction after treatment with 10 μg/ml 3-CPs plus a constant dose of 365 nm light is independent of incubation time with the drug before irradiation within the limits of statistical variation. One minute incubation already exerted about the maximum effect. It was established that, for the doses of 365 nm light used, there is no sensitizing effect after washing. Consequently, this compound was very loosely bound in the dark.

Our experience showed that the 3-CPs is light sensitive and therefore must be protected against light. Indeed thin layer and paper chromatography, as well as fluorescence spectra of illuminated 3-CPs in aqueous solutions, demonstrate the presence of a highly fluorescent photoproduct with the characteristics of 4',5'-dihydropsoralen.

Due to the formation of such photoproduct(s) we noticed a decline in the photobiological activity of 3-CPs when it is previously exposed to light.

It was also shown that 3-CPs binds to DNA in vitro and in vivo (tables 1 and 3) in the presence of 365 nm light. The efficiency of this binding appears to be higher in vivo than in vitro in spite of the fact that the concentration in µg of DNA per ml is higher in vitro. However, the conditions are not strictly comparable, the configuration and local concentration and DNA are likely to play an important role. Moreover, a metabolic activation is not entirely excluded.

Similar to other photoactive furocoumarins 3-CPs binds not only to DNA but also to RNA (table 3). For 8-MOP the photoreactivity with RNA is found to represent 61 to 87% of that with DNA.

Consequently, on a molecular basis the photoaffinity of 3-CPs to DNA is much higher than to RNA. This feature clearly distinguishes 3-CPs from 8-MOP, psoralen and angelicin.

In order to compare the photoaffinities of 3-CPs and 8-MOP to DNA, the following points have to be considered. (a) it is known that furocoumarins, including 8-MOP, bind specifically to pyrimidines; from the structure of 3-CPs one can reasonably assume that this molecule reacts in the same manner; (b) the total number of pyrimidine per haploid yeast genome equals $2.1 \times 10^7$.

For a dose of $18.9 \times 10^3$ J/M$^2$ and $5 \times 10^{-5}$ M of 8-MOP or 3-CPs, $0.5 \times 10^6$ molecules of 8-MOP or $10.5 \times 10^6$ molecules of 3-CPs are linked to DNA per cell. On average the binding ratio is 1 molecule of 8-MOP over 42 pyrimidine bases and 1 molecule of 3-CPs over 2 pyrimidine bases. For 8-MOP this ratio is probably an underestimation since a fraction of the 8-MOP molecules is bound as cross-links and a 1 over 30 ratio is more likely to reflect the real binding. In comparison to 8-MOP the photoaffinity of 3-CPs to DNA is strikingly high, about 15 times more 3-CPs is linked to DNA, as compared to 8-MOP. However, other examples of such a high photoreactivity among the furocoumarin derivatives are known. The 4,5',8-trimethylpsoralen, for instance, is about 12 times more reactive with DNA in vitro than 8-MOP. If this compound has a higher photoreactivity in vivo than in vitro as shown here for 8-MOP and 3-CPs, the photoreactivity in vivo found for 3-CPs in vivo certainly lies in the same range.

DNA containing interstrand cross-links are characterized by a capacity to renature in slow cooling after a heat denaturation. An absence of cross-link formation, at least in the dose range used in our experiments, is shown by the inability to renature DNA previously treated with 3-CPs and 365 nm light. This is in contrast to 8-MOP. Consequently, 3-CPs exhibits only monofunctional properties.

In the biological tests of the 3-CPs activity, the controls show that the contribution of the 365 nm light alone in killing was negligible. The small lethal effect in wild type is unlikely to be due to 365 nm light-induced pyrimidine dimers since (a) a UV-sensitive excision-deficient mutant, rad$_{2-20}$, is not sensitive to 365 nm light up to doses of $25.2 \times 10^3$ J/m$^2$; (b) the light doses used here are much lower than those needed to induce pyrimidine dimers in Escherichia coli. Other known effects of near-UV light, such as the inhibition of protein synthesis in yeast, may account for such a killing.

In Saccharomyces, 3-CPs is taken up and washed out as readily as 8-MOP. Differences seen in the lethal effects of the two drugs are not due to differences in uptake and excretion, but to different photoreactivities of the drugs.

For a given survival level the concentration of 3-CPs versus 365 nm light dose in a log-log plot follows a linear function for wild type and rad$_{9-4}$. This indicates that there is no reciprocity between the light dose and the drug concentration for cell killing; a reduction in concentration of the drug by a factor of 10, for instance, does not require an enhancement of the light dose by the same factor to induce an equal killing effect. In other words, the efficiency of light activation of the drug increases when the concentration is reduced. At a high concentration of 3-CPs, this is likely to be due either to the absorption of the 365 nm light by the unbound molecules of the drug, producing a shielding effect, and/or to the formation of photobiologically inactive 3-CPs photoproducts (see above). Since the dose-modifying factor for rad$_{9-4}$ (as compared to wild type) is constant, the higher photosensitivity of the mutant cannnot be explained by a difference in the physical interaction between light and the drug. It has been shown that cells are more photosensitized by a bifunctional agent like 8-MOP than by monofunctional compounds, such as 3-CPs or angelicin. The survival response between 3-CPs and 8-MOP differs by a factor of 6, whereas the photoreactivity of the two drugs with DNA differs by a factor of 4.8 in vitro (table 3) and by a factor of 15 in vivo (see above). In other words, the resistance to the killing effect of 3-CPs, as compared to that of 8-MOP, is much higher than that expected from the photoreactivity. This difference is very likely to be due to the presence of cross-links in 8-MOP plus 365 nm light treated cells and to the fact that monoadditions are very efficiently repaired. Indeed it has been recently demonstrated in Escherichia coli that this last type of lesions is easily repaired.

We have seen that 8-MOP and 3-CPs have a relatively low photoaffinity for RNA. Angelicin is known to bind equally well to DNA and RNA. This implies that, at equal concentrations of the 3 drugs and identical doses of light, a fewer number of angelicin molecules will be bound to DNA, as compared with 8-MOP or 3-CPs. The amount of damage in genetic material being lower, a higher survival is espected with angelicin.

The difference in shape of the survival curves for the three compounds is difficult to explain at the moment. However, the exponential survival curve seen for 3-CPs does not seem to be a general feature of monofunctional furocoumarins.

A synergistic interaction between the repair pathway controlled by rad$_2$ and rad$_9$ is found for 3-CPs plus 365 nm light induced lesions. This is in contrast to 8-MOP, for which an additive interaction was found; this was interpreted as due to the repair of two different substrates, i.e. the monoadducts and cross-link. The synergism seen for 3-CPs plus light induced damage indicates that the two repair pathway act on one single type of lesion likely to be the monoadducts induced.

In agar holding experiments (AHR) it has been shown that a strain defective in excision is unable to perform a dark repair for both 3-CPs and 8-MOP. A strain defective in recombination has a reduced capacity to repair 3-CPs plus 365 nm light induced damage. Consequently, it appears that the excision repair pathway in wild type and rad$_{9-4}$ cells is essential in AHR for both compounds. In wild-type cells the same kinetics of AHR are observed for 3-CPs, 8-MOP, angelicin and psoralen. This implies that one type of lesion, commonly induced by these four compounds (monoadducts), is subject to agar-holding recovery.

In vivo experimentation on animals and toxicity studies

A systematic in vivo experiment was performed in order to compare an eventual cancerogenic effect of psoralen and psoralen bi-functional derivatives, such as 8-MOP, with 3-CPs.

These experiments were effected on the skin of homozygote albino mice strain XVII nc/Z (Institut du Radium Orsay), which exhibit a particularly low ratio of spontaneous skin tumor (less than 0.05%).

The experiments were effected on groups of 40 mice, male and female.

After having been submitted to chronic topical applications of psoralen on the two ears, followed by 365 nm U.V. irradiation, the animals had significant cutaneous reactions, such as an erythema, followed by intensive chronic inflammation even followed by necrosis of more or less significant parts of treated tissues.

The development of tumors on ears is dose dependent. After 24 applications (cumulative dose of $4.5 \times 10^5$ J/m$^2$) only 3% of the animals developed a tumor on ears.

After 115 topical applications of psoralen, followed each time by 10 minutes of irradiation (cumulative doses of $2.07 \times 10^6$ J/m$^2$), 100% of the animals developed a tumor; 50% having tumors on two ears.

The same treatment effected with 3-CPs, i.e. 115 applications on the two ears, 30 minutes of rest and 10 minutes of irradiation, revealed neither erythema nor cutaneous inflammation nor any tumor. Neither macroscopic nor microscopic reaction was observed during 450 days of observation. No animal died. 3-CPs was also tested intraperitoneally (36 injections of 0.4 mg each over a period of 7 weeks). All the animals remained alive, without any decrease in weight or other sign of toxicity.

As the clinical oral dose is of about 0.6 mg/kg, the dose of 0.4 mg for the mice represents about 30 times the dose classically administered to humans.

The essential advantage of compounds (I) and, more particularly, of 3-CPs is obvious from the rated results.

In all these experiments the U.V. lamp was of the type of HPW 125 W, manufactured by Philips.

EXAMPLES

I. In order to experiment with 3-CPs on patients having psoriasis, this compound was prepared as follows:

A mixture of 0.162 g (1.00 mmol) of 5-formyl-6-hydroxybenzofuran (prepared as indicated by L. R. Worden et al. in the *Journal of Organic Chemistry*, Vol. 84, No. 8, August 1963n, p. 2311-2313) and 2.0 ml of absolute ethanol was warmed to effect solution of the benzofuran, and then 0.18 ml (1.2 mmol) of diethylmalonate and 0.03 ml of piperidine were added to produce an accompanying red coloration. This reaction mixture was heated under reflux for 15 min. and allowed to cool, whereupon the product crystallized. Filtration furnished 0.216 g (84%) of orange plates, mp 151°-152° C. Two recrystallizations of a small portion from methanol for analysis gave long orange needles of mp 153°-154°.

Anal. Calculated for $C_{14}H_{10}O_5$: C 65.12; H 3.90
found: C 65.04; H 4.22

The effectiveness of thus-obtained 3-CPs was tested on 10 patients having ordinary psoriasis covering from 200 to 400 cm$^2$ of skin.

Preparation of 1% 3-CPs ointment:

1 g of 3-CPs was ground to a very fine powder and then dispersed in 70 g of "HYDROCERINE" (a commercially-available product manufactured by ROC) at 70° C. 29 ml of water were added at 70° C. in order to obtain an aqueous emulsion in oil.

The composition of the ointment was consequently, the following

Hydrocerine 70%
water 29%
3-CPs 1%

It was possible to add a preserving agent, such as methyl p-hydroxybenzoate in a quantity of about 0.1%. Such a preserving agent was preferably added to water prior to adding said the water to HYDROCERINE.

When the psoriasis lesions were very keratosic, a preliminary cleaning or fettling was effected with, for example, salicylated vaseline.

For all the patients the ointment containing 3-CPs was applied on all the lesions but one, in order to prove the specific and not placebo activity.

The irradiation dose at 365 nm UV was of about 5 J/cm$^2$ per unit treatment and administered using the usual PUVA therapy set-up.

It was noted that the action of 3-CPs is slower than that of 8-MOP but, as 3-CPs produced no erythema or cutaneous inflammation, it was possible to perform two daily treatments or even to increase the irradiation dose up to 20 J/cm$^2$.

With four applications per week, restoration was obtained in about 20 weeks to about 40 weeks.

With two treatments per day, restoration was obtained after 20 to 40 applications. As a continuing treatment, it was possible to perform from 2 treatments per week to 1 per month with an average of 1 treatment per week.

II. A similar experiment was made, but using 3-cyano-psoralen ($R_1 = -CN$, $R_2 = -H$).

1.62 g of formyl-5-hydroxy-6-benzofuran were dissolved in 30 ml of ethanol. 1.47 g of ethyl cyanoacetate and 400 mg of piperidine were added, followed by a heating step under reflux for 30 minutes.

Yellow micro-crystals were obtained after cooling, filtering, drying, recrystallization in acetonitrile and subsequent sublimation under 10 mm pressure.

MP = 259° C.

Analysis $C_{12}H_5NO_3$ Calc % C 68.24; H 2.37; N 6.63.
Found C 67.91; H 2.54; N 6.78.
NMR (CDCl$_3$)δH-4 9.08 ppm
I.R. (in KBr)ν—C≡N: 2210 cm$^{-1}$ III. A similar experiment was performed, but using 3-carbomethoxypsoralen ($R_2 = -H$, $R_3 = -CH_3$)

1 g of formyl-5-hydroxy-6-benzofuran (prepared according to the method of L. R. Worden et al-*J. Org. Chem.* 84, 2311-2313, and that of P. Queval and E. Bisagni, *Eur. J. Med. Chem. Chim. Ther.*) was dissolved in 20 ml of ethanol. 1 ml of dimethylmalonate and 200 mg of piperidine were added, and the mixture was heated under reflux for 30 minutes.

The solid obtained after cooling was dry-filtered and recrystallized in a small quantity of ethanol, and yellow needles were obtained:

MP = 191°–192° C.

Analysis $C_{13}H_8O_5$: Calc.: % C 63.94; H 3.30. Found: % C 63.87; H 3.47

NMR (DMSO)δH-4: 8.86 ppm

I.R. (in KBr)$\nu$-C=O: 1745 and 1695 cm$^{-1}$.

IV. A similar experiment was performed by using 3-carboethoxy-8-methylpsoralen ($R_2 = -CH_3$, $R_3 = -CH_2CH_3$), prepared according to the method of P. Queval and E. Bisagni, *Eur. J. Med. Chem.*, precited.

MP = 188° C.

IR: $\nu-C=O$ (ester), 1 730 cm$^{-1}$; $\nu-C=O$ β pyrone 1 750 cm$^{-1}$; $\nu-C=C$ 1 620 and 1 590 cm$^{-1}$.

V. In order to compare the activity of the compounds of the invention with compounds having an analogous structure $[R_2 = -H, R_3 = -C(CH_3)_3]$ psoralen 3-t-butylcarboxylate was prepared according the precited method and recrystallized in cyclohexane.

MP: 162° C.–164° C.

Analysis: Calc % C 67.12%; H 4.93% found % C 66.94%; H 4.97%.

This compound was found to be inactive.

We claim:

1. A method of treating psoriasis by administering to a patient afflicted therewith an effective amount of a therapeutically-acceptable composition comprising carrier and an effective amount of a monofunctional derivative of psoralen of the formula

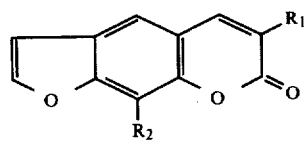

wherein
$R_1$ is —COOR$_3$ or —CN,
$R_2$ is —H or —CH$_3$, and
$R_3$ is —H, —CH$_3$ or —CH$_2$CH$_3$,
in conjunction with a sufficient dose of 356 mm U.V. irradiation.

2. A method of claim 1 wherein the average irradiation dose is from about 5 J/cm$^2$ to 20 J/cm$^2$ per unit treatment.

3. A method of claim 1 wherein the average irradiation dose is from about 10 J/cm$^2$ to 15 J/cm$^2$.

4. A method of claim 1 for topical application wherein the amount of psoralen derivative is from about 0.5% to about 4% of the composition.

5. A method of claim 4 wherein the amount of psoralen derivative is from about 1% to about 2% of the composition.

6. A method of claim 1 for oral treatment wherein the quantity of psoralen derivative is from about 1 mg to about 2 mg per kg of weight of the patient.

7. A method of claim 1 wherein R$_1$ is —CN and R$_2$ is —H, the psoralen derivative being 3-cyanopsoralen.

8. A method of claim 1 wherein R$_1$ is —COCH$_3$ and R$_2$ is —H, the psoralen derivative being 3-carbomethoxypsoralen.

9. A method of treating psoriasis according to claim 1, wherein
R$_1$ is —COOR$_3$ or —CN;
R$_2$ is —H and
R$_3$ is —CH$_3$,
in the formula of a monofunctional derivative of psoralen.

10. A method according to claim 1 wherein the psoriasis is psoriasis punctata.

11. A therapeutically-acceptable ointment composition for treating psoriasis and containing carrier and an effective amount of a compound of the formula

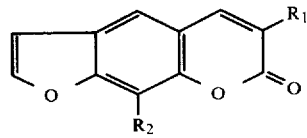

wherein R$_1$ is —COOR$^3$ or —CN; R$_2$ is —H and R$_3$ is —CH$_3$.

12. A method for treating psoriasis which comprises administering to an afflicted subject an effective amount of a composition according to claim 11 in conjunction with an effective dose of 365 nm U.V. irradiation.

13. A therapeutically-acceptable ointment composition useful, in conjunction with effective exposure to near-ultraviolet light, for treating psoriasis, the composition comprising carrier and an effective amount of a monofunctional derivative of psoralen of the formula

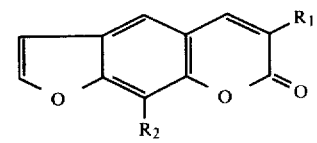

wherein
R$_1$ is —COOR$_3$ or —CN,
R$_2$ is —H or —CH$_3$, and
R$_3$ is —H, —CH$_3$ or —CH$_2$CH$_3$.

14. A composition of claim 13 containing from about 0.5% to about 4% of the psoralen derivative.

15. A therapeutically-acceptable ointment composition containing carrier and from about 0.5 to about 4 percent by weight of a monofunctional derivative of psoralen of the formula

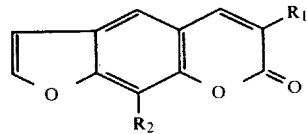

wherein
R$_1$ is —COOR$_3$ or —CN,
R$_2$ is —H or —CH$_3$, and
R$_3$ is —H, —CH$_3$ or —CH$_2$CH$_3$.

16. A composition of claim 15 containing from about 1% to about 2% of the psoralen derivative.

* * * * *